United States Patent
Lotti et al.

(10) Patent No.: US 8,163,180 B2
(45) Date of Patent: Apr. 24, 2012

(54) PROCESS AND INSTALLATION FOR ANAEROBIC TREATMENT OF MATERIAL HAVING HIGH SOLIDS CONCENTRATION

(75) Inventors: Jean-Pierre Lotti, Valergues (FR);
Helene Fruteau De Laclos, Jacou (FR);
Claude Saint-Joly, Sussargues (FR)

(73) Assignee: Valorga International, Montpellier (FR)

( * ) Notice: Subject to any disclaimer, the term of this patent is extended or adjusted under 35 U.S.C. 154(b) by 291 days.

(21) Appl. No.: 12/514,721

(22) PCT Filed: Nov. 13, 2007

(86) PCT No.: PCT/FR2007/052332
§ 371 (c)(1),
(2), (4) Date: Sep. 14, 2009

(87) PCT Pub. No.: WO2008/059167
PCT Pub. Date: May 22, 2008

(65) Prior Publication Data
US 2010/0044307 A1 Feb. 25, 2010

(30) Foreign Application Priority Data

Nov. 13, 2006 (FR) .................................. 06 54872
Jan. 5, 2007 (FR) .................................. 07 52530

(51) Int. Cl.
*C02F 3/28* (2006.01)
*C02F 11/04* (2006.01)
(52) U.S. Cl. ...................................... 210/603; 210/259
(58) Field of Classification Search .................. 210/605, 210/621, 629, 630, 252, 259, 603
See application file for complete search history.

(56) References Cited

U.S. PATENT DOCUMENTS
6,171,499 B1 * 1/2001 Bouchalat .................... 210/603

FOREIGN PATENT DOCUMENTS
FR  2551457 A2  3/1985
FR  2935372 A1 * 3/2005
WO 2005/077841 A1 8/2005

OTHER PUBLICATIONS
International Search Report of PCT/FR2007/052332, date of mailing Sep. 19, 2008.

* cited by examiner

*Primary Examiner* — Fred Prince
(74) *Attorney, Agent, or Firm* — Westerman, Hattori, Daniels & Adrian, LLP

(57) ABSTRACT

The invention relates to a process for anaerobic treatment of material having a solids concentration greater than 15% in a digester in the form of a sealed tank (1) equipped with means (2) for supplying material to be treated and means (3) for discharging digested material and also vertical homogenization means (6) in the form of injectors for injecting a gaseous fluid into the bottom (7) of the tank (1). Through distribution in the tank (1) of the material supply means (2) relative to the discharge means (3) and using vertical homogenization means (6) that guarantee the homogeneity of the material treated by vertical sectors (8) in the tank, conferred on the material in the tank (1) is a forced unidirectional circulation that is uniform throughout the entire cross section of this tank, and along one substantially horizontal component, between said supply means (2) and said discharge means (3). The invention also relates to an installation for implementing such a process.

11 Claims, 3 Drawing Sheets

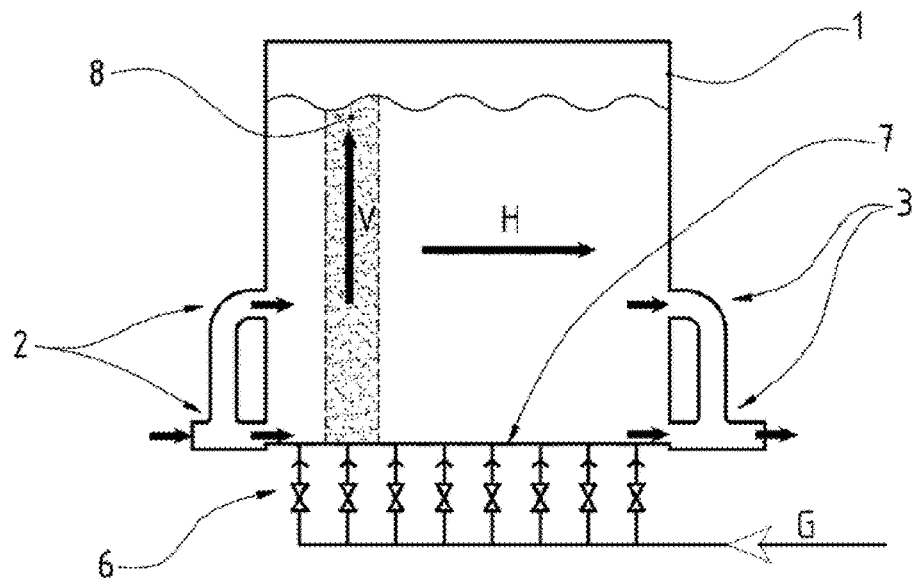
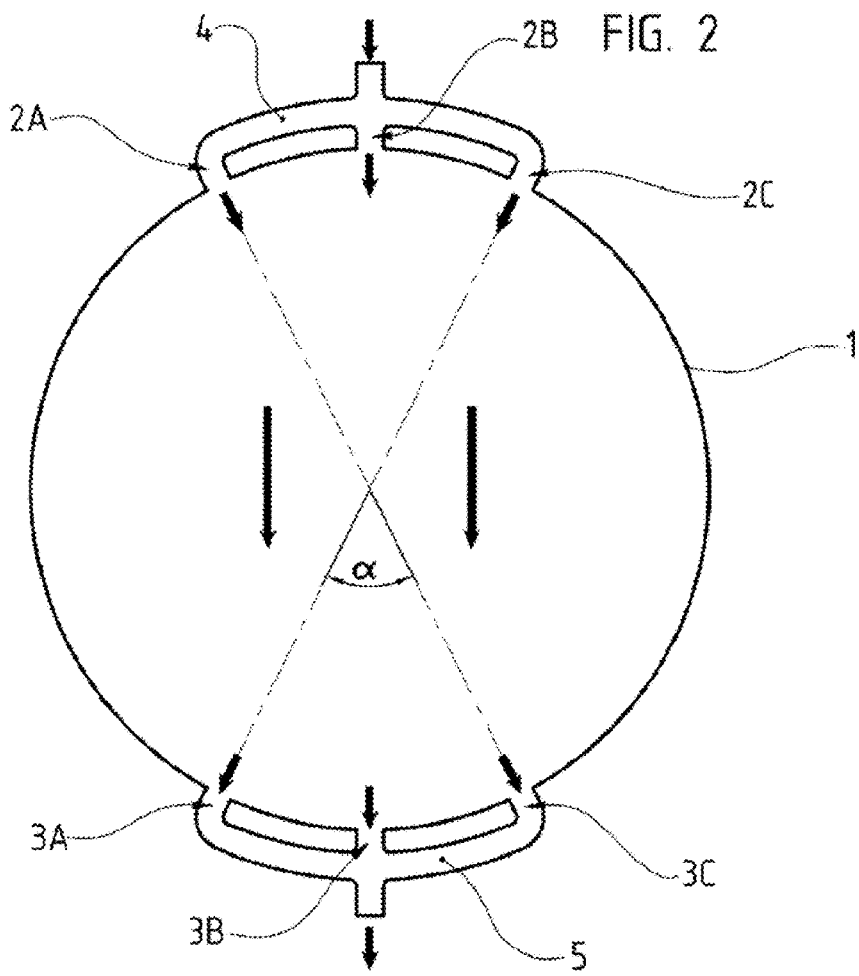

PROCESS AND INSTALLATION FOR ANAEROBIC TREATMENT OF MATERIAL HAVING HIGH SOLIDS CONCENTRATION

BACKGROUND OF THE INVENTION (1) Field of the Invention

The invention relates to a process and an installation for anaerobic degradation of waste containing organic solids, in the form of a paste having a high solid concentration, in any case higher than 15%, and in particular ranging between 25% and 30%.

The present invention relates more particularly to the field of the anaerobic degradation of waste formed of heterogeneous organic solids which can contain undesirable particles, in particular heavy and non-organic particles, likely to settle in a fermentation tank, such as for example stones, glass or metal compounds.

(2) Description of the Prior Art

Solid organic waste the degradation of which is the objective of the present invention is previously prepared in the form of a paste with high solid concentration, whereby said paste may be fibrous, but in any case compact.

In the field of the anaerobic degradation of effluents with low solid content, which are hence more liquid than pasty, are known processes for anaerobic degradation using adapted tanks.

FR 2 510 605 for example discloses a process and an installation for degradation in wet anaerobic medium of organic products, by-products and waste, comprising a reactor having a cylindrical fermentation tank vertically divided into two parts by a central partition. The first part is connected by a siphon to a supply well and the second part is connected by a siphon to a discharge well for the material. The supply and the discharge of the products occur through pneumatic thrust.

FR 2 530 659 takes this same structure and proposes to improve it by submitting the effluents to a direction of tormented circulation inside the tank, while providing biogas injection through short and successive jets through conduits ending onto the bottom of the tank.

According to an embodiment of the tank described in these documents, the supply and discharge wells are located in the vicinity of each other, the above mentioned partition being arranged vertically between the two openings of said well ending into the reactor. This partition has a width smaller than the width of the tank and a height smaller than the height of the tank, the bottom of the tank having a double slope having substantially the shape of an ellipse.

According to another embodiment of the tank also described in these documents, the above-mentioned supply and discharge wells are substantially diametrically opposite each other, the vertical partition separating the fermentation tank substantially diametrically, with a height smaller than the height of the tank and leaving communicating passages between the two compartments in the upper and lower portions in order to favour an upward movement of the material in the first portion and a downward movement in the second portion, the bottom of the tank having one single slope.

Even more specifically, FR 2 551 457 proposes to subdivide the enclosure into a plurality of sectors through intermittent injection of biogas, taken from an appropriate storage tank, into each one of said sectors under a predetermined pressure and time period. The biogas is re-injected into each sector successively, i.e. shifted in time, so as to achieve a rotation of the biogas injection into the enclosure, from one sector to the next one.

Finally, FR 2 577 940 proposes to remove the material-supply and discharge wells in order to reduce the construction costs. In this case the products to be degraded are injected directly into the enclosure, preferably towards the bottom of said enclosure, and the exit of the degraded products occurs by gravity. The mechanical thrust is carried out by a pump for thick material, preferably with piston or screw.

One of the disadvantages of the prior known solutions lies in the complexity of the digesters resulting from same. In particular, the manufacture of these digesters is expensive, because of the constraints of internal partitioning and the specific designs of the means for supplying and discharging effluents.

Indeed, when such digesters are used with a paste having a high solid concentration, the partitions carried out must have high mechanical strength because of the pressures exerted by the thick paste in movement. This results into high manufacturing costs.

In fact, the manufacturing constraints on the state-of-the-art digesters increase according to the increase of the size of the tank of the digester.

It also appears from this statement of the state of the art that one of the problems not perfectly solved by the existing processes and digesting devices is the control of a homogeneous circulation of the material to be digested between the supply and discharge paths.

The circulation of the material in the form of effluents occurred so far through partitioning and a tormented control of the flow of effluents inside said tank.

SUMMARY OF THE INVENTION

The present invention pretends to cope with these disadvantages of the state of the art through a finally very simple process and installation.

To this end, the invention relates to an process for anaerobic treatment of material with a high solid concentration, i.e. higher than 15%, in a digester in the form of a closed tank provided with means for supplying material to be treated and means for discharging the digested material as well as means for vertical homogenisation in the form of gaseous-fluid injectors on the bottom of the tank, wherein, through a distribution at the level of the tank of the means for supplying material with respect to the discharge means and through the means for vertical homogenisation guaranteeing the homogeneity of the material by vertical sectors in the tank, a uniform forced unidirectional circulation is imparted to the material in the tank over the full cross-section of the latter, and according to a substantially horizontal component, between said supply means and said discharge means.

Advantageously, the internal space of said tank is cut into vertical sectors by the arrangement of the homogenisation means and the vertical sectors are homogenized intermittently and successively by the homogenisation means.

A preferred extraction of the settled particles in the lower portion of the tank and/or a recirculation of the material between the discharge means and the supply means can also be performed.

According to another feature, this recirculation can occur during short periods of time.

The invention also relates to an installation for implementing the process, comprising a digester in the form of a closed tank provided with means for supplying material to be treated and means for discharging the digested material as well as means for vertical homogenisation in the form of gaseous-fluid injectors on the bottom of the tank, wherein the means for supplying material are arranged at the level of the tank diametrically opposite the means for discharging the digested material, and, in combination, the means for vertical homogenisation are comprised of gaseous-fluid injection ramps extending in the bottom of the tank transversely to the substantially horizontal direction of flow of material in the tank.

According to another feature, the means for supplying material and the means for discharging the digested material are arranged to an arc of a circle on the circular cross-section of the tank. They can also be arranged at different heights of the tank.

The gaseous-fluid injectors are advantageously arranged on slopes parallel to each other and perpendicular to the direction of advancing of the material in the tank.

The installation can also comprise a device for discharging the digested material, in particular a device allowing their additional dehydration.

According to another feature, the installation can in addition comprise a circuit for re-circulating the material between the discharge means and the supply means.

The invention thus permits to treat under favourable conditions, by digestion, heterogeneous organic solids, for example domestic and comparable waste (urban, industrial, agricultural waste, etc), having a high solid content, for example about 25% to 30%.

Thanks to the present invention the construction of the installation will be simplified and the manufacturing cost will be radically reduced. Furthermore, a broader range of material will be usable for said construction.

Other objectives and advantages of this invention will become clear from the following description. The understanding of this description will be facilitated when referring to the attached drawings.

BRIEF DESCRIPTION OF THE DRAWINGS

FIG. 1 is a schematic and elevation view of a tank according to a first variant of embodiment, FIG. 2 is a schematic view of the cross-section of a tank forming a digester according to the installation of the invention.

DETAILED DESCRIPTION OF THE PREFERRED EMBODIMENTS

Figure 3:
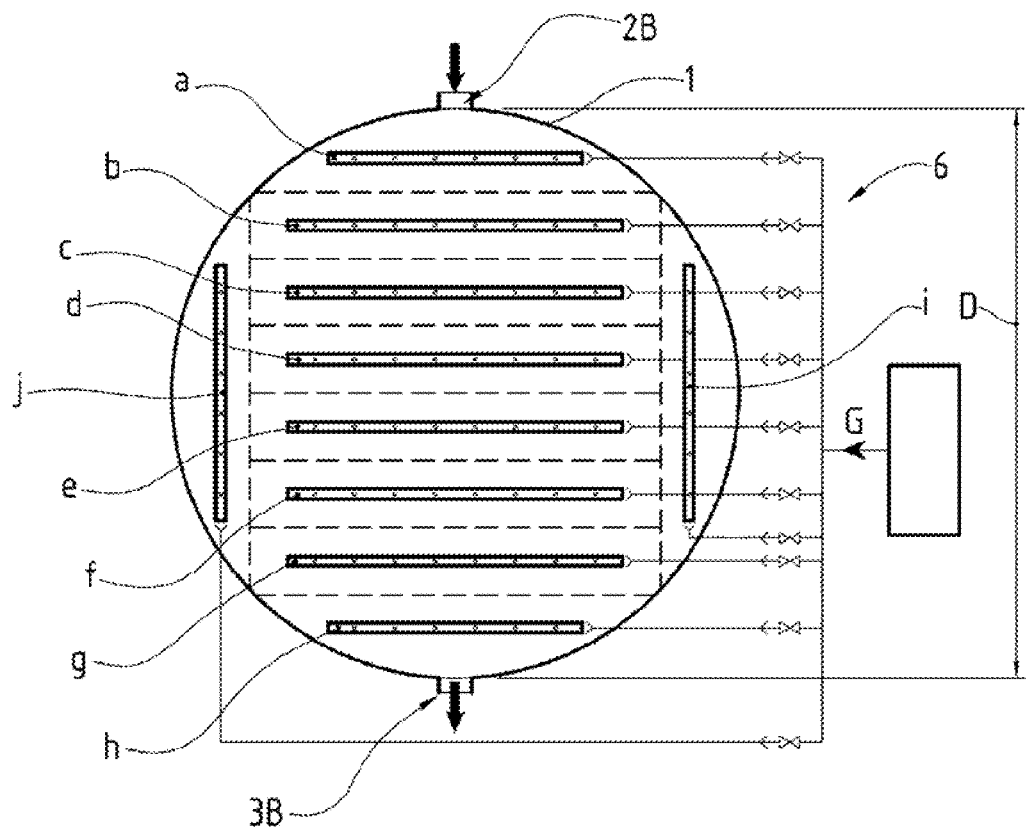
FIG. 3 is a schematic view representation of the gaseous-fluid injecting ramps extending on the bottom of a tank.

As can be seen in the figures of the attached drawings, the present invention relates to a process and an installation for anaerobic treatment of waste having a high solid concentration. In this connection, it should be noted that the invention specifically relates to the treatment of such waste containing organic solids, in the form of a paste having a high solid concentration, in any case higher than 15%, and in particular ranging between 25% and 30%, and thus comprised of material having a low water content.

The solid organic waste the degradation of which is the objective of the present invention is previously prepared, in particular by the addition of a liquid, for example water resulting from the dehydration of the digested material, in the form of a paste with a high solid concentration, whereby said paste can be fibrous, but in any case compact.

This waste can in addition, without this being systematic, contain non-organic heavy particles likely to settle in a fermentation tank.

Its high solid concentration provides the paste to be treated within the framework of the invention with such a viscosity that the settling phenomena, even if they exist, are limited.

Since the material used is in the form of a paste, the terms "material" and "paste" will thus indifferently be used generically to denote all this material likely to be treated by means of the present invention.

According to the process of the invention, the anaerobic degradation of organic solids with a high solid content, in any case higher than 15%, and in particular ranging between 25% and 30%, is carried out in an installation comprising a vertical cylindrical fermentation tank 1, without any partition, as well as all the internal mechanical equipment.

At the level of this tank 1 are provided for means for supplying 2 the material to be treated and means for discharging 3 the digested material, means 2 and 3 being formed of supply 2 and discharge openings 3, respectively.

As shown in FIGS. 1 and 2, the supply 2 and discharge openings 3 are arranged so as to maintain a unidirectional forced advancing of the material in a substantially horizontal plane, and over a major portion of the cross-section of the tank 2. Indeed, opening or openings 2 for supplying the material to be treated are placed at the level of the wall of this tank 2, having a circular form, substantially diametrically opposite to the opening or the openings for discharging 3 the fermented material. A unidirectional forced circulation is thus imposed on the material under fermentation in a horizontal direction thanks to a supply by thrust, preferably achieved by means of a pump, for example with a piston or screw.

FIG. 2 shows a preferred embodiment of such a tank 1, where the supply openings 2A, 2B, 2C as well as the exit openings 3A, 3B, 3C are distributed over an arc of a circle the inscribed angle α of which, in any case smaller than 180°, is so determined that the material entering into the tank is distributed over a large surface of the cross-section of the tank. The direction of circulation of the material is shown by means of arrows.

Advantageously, the openings 2A, 2B, 2C, on one side, and 3A, 3B, 3C, on the other side, are connected by single conduits 4 and 5, in order to ensure a uniform supply and/or exit flow rate of the material through these openings, and to achieve similar speeds of progression of the material over the full cross-section of the tank.

On the other hand, as shown in FIG. 1, the supply 2A, 2B, 2C and/or exit openings 3A, 3B, 3C can advantageously be distributed at different heights on the wall of the tank.

The circulation is in addition favoured by homogenisation means 6 in the form of pipes 6 for injecting gaseous fluid under pressure at the level of the bottom 7 of the tank 1.

One understands that the injection of gas under pressure induces a homogenisation by vertical sectors 8 in the tank, by imparting an ascending vertical movement to the material over the full height of the tank 1. The vertical sectors 8 considered are defined by the location of the injecting pipes and advantageously adopt the shape of parallel sections.

The homogenisation means 6 are an essential element in the operation of the process and the installation according to the present invention. In FIG. 1 are shown the two components of the movement of the material under fermentation: horizontal progression H and the vertical movement V.

The horizontal progression H is achieved under the action of the thrust of the supply of the material to be treated.

The vertical movement V, favouring the fact that the material under treatment do not settle, is produced by the injection of fluid, in particular gas, under pressure G at the bottom of the tank.

Advantageously, the pressure of injection of the fluid at the bottom of the tank is higher than or equal to twice the static pressure in the tank. For example, for a material height of 20 meters inside the tank, the pressure of injection is higher than or equal to 4 bars.

As a matter of fact, by limiting the settling in a sector and in the tank in general, and by decreasing the risk for differential speeds of circulation to be created between the material, in particular inside one and the same sector 8 and in the tank in general, the means for vertical homogenisation contribute to the homogeneous advancing of the material injected into the tank, this advancing corresponding globally to that of the vertical sectors 8.

The virtual division of the tank 1 into several sectors 8 occurs through the distribution of the injecting pipes 4 on the bottom of the fermentation tank 1. Each sector 8 is individually supplied with gas under pressure. The gases are injected successively into each sector 8 and shifted in time.

FIG. 3 shows in particular the arrangement of these sectors 8. The latter are arranged so that the bottom of the tank is virtually divided by ramps, numbered a to h, parallel to each other and perpendicular to the direction of progression of the material in the tank 1, in short perpendicular to the plane D connecting the median supply 2B and discharge openings 3B. Thus, the injection into each sector 8 successively occurs from the ramp a on the side of the supply openings 2A, 2B, 2C towards the ramp h on the opposite side corresponding to the discharge openings 3A, 3B, 3C, favouring a movement in the direction of the forced unidirectional and horizontal circulation of the material.

Advantageously, ramps i and j perpendicular to the preceding ramps and located on the edges of the tank 1 complement these homogenisation means 6. This can prove particularly favourable for the tanks having a very large volume, by limiting the idle volumes in the digestion tank 1, which is essential for the proper operation of the process and the installation for the implementation of the process.

Generally speaking the absence of partitioning constitutes, in the invention, an advantage for the circulation of the material. From an economic point of view, this absence also results into a reduction of the manufacturing cost of the tank 1.

Figure 4:
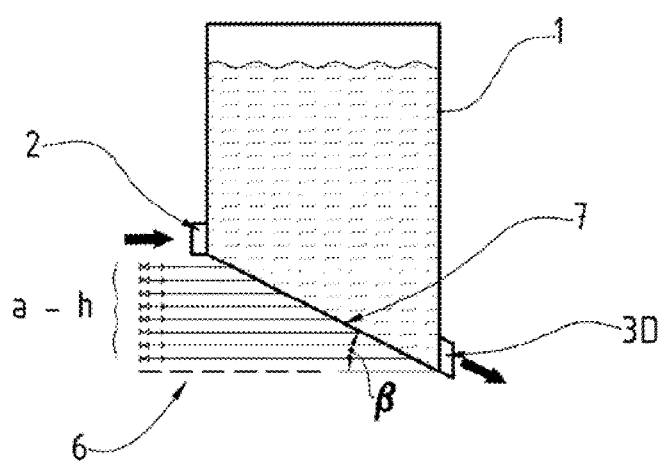
FIG. 4 is a schematic and elevation view of a tank according to a second variant of embodiment.

According to a second variant of embodiment of a tank 1 shown in FIG. 4, the bottom 7 of the tank 1 has a slope β, said slope β being so oriented that the material under fermentation, and in particular, if these are present, the heavy particles eventually settled on this bottom of the tank, move by gravity from the supply opening or openings 2A, 2B, 2C to the discharge opening or openings 3A, 3B, 3C. The angle of the slope β is adjusted with the nature and the grain-size distribution of the paste to be treated, so that the conveying is progressive and compatible with the transformation of the organic material under the action of fermentation.

Advantageously, at least one 3D of the discharge openings is located in the lower portion of the wall of the tank 1 so that, if heavy particles are accumulated at the lower level of the bottom 7 of the tank 1, they leave the enclosure by gravity.

According to this second variant of embodiment, the pipes 6 through which the fluid under pressure is injected extend horizontally on the inclined bottom 7 of this tank 1 and so that the fluid is directed in the same direction as the conveying of the material. The advantages of this arrangement are stated hereafter. Firstly, this arrangement permits to create in the perimeter close to the pipe a pneumatic thrust in the direction of the circulation of the material, which favours the transverse advance of said material and in particular of the heavy particles eventually settled on the bottom 7 of the tank 1. Secondly, the penetration by gravity of these heavy particles into the opening of the pipes 6 is thus avoided.

Figure 5:
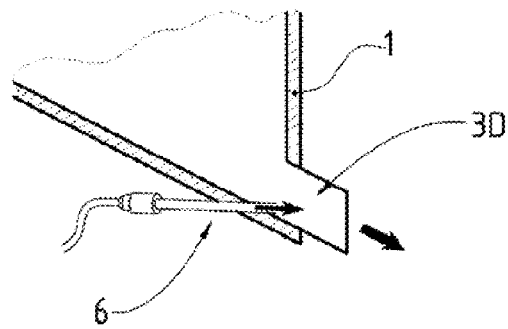
FIG. 5 is a view of a particular arrangement of a gaseous-fluid injector at the level of a material-discharge opening located in the lower portion of a tank.

Injecting pipes 6 for fluid under pressure will advantageously be arranged in front of the discharge opening or openings 3D located at the lower level of the tank 1, as shown in FIG. 5. In this way, through these pipes 6 a mechanical or pneumatic action in order to free, should the case arrive, the whole or part of the opening or openings 3D, within the framework of the maintenance of the installation, is allowed without any direct intervention on said openings likely to represent a major disturbance of the operation of the present device and process.

According to another feature, the present invention takes advantage of the geometry of the tank 1 to perform, on the one hand, an extraction and, on the other hand, a recycling by gravity of the fermented material.

Thus, the process according to the invention also allows a preferred extraction of the heavy inert materials eventually settled at the lower level of the fermentation tank.

It is recalled in this respect that the process and device according to the invention are intended at treating material formed of heterogeneous solid organic waste that may contain undesirable particles likely to settle in a fermentation tank, such as for example stones, glass or metal compounds.

Figure 6:
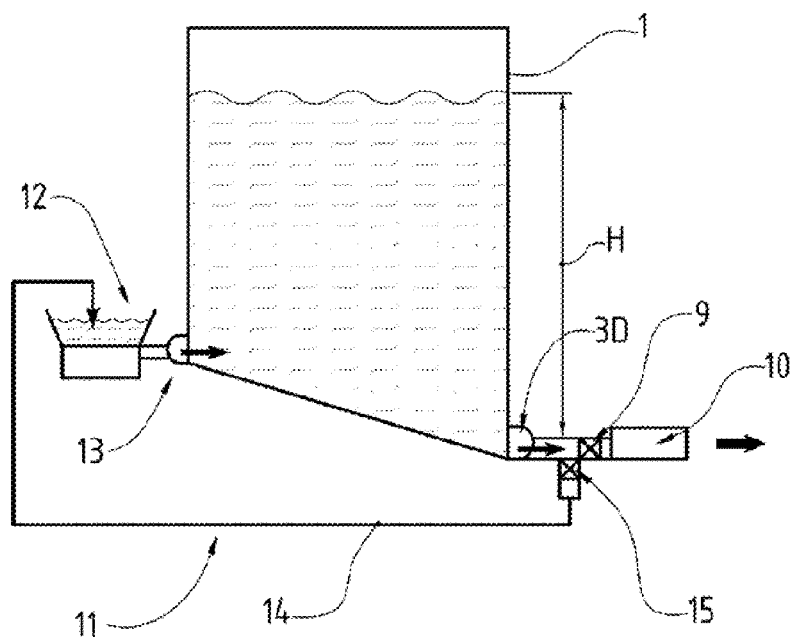
FIG. 6 is a schematic and elevation view of a tank provided with means for accelerating the material in the tank.

As shown in FIG. 6, at least one exit opening 3D is connected through a valve 9 to a device 10 allowing the discharge of the digested material, advantageously designed in the form of a device 10 allowing their additional dehydration.

It is recalled in this respect that water proceeding from this dehydration can be used for the preparation of the solid organic waste the degradation of which is aimed by the present invention, for the preparation of the paste, which the installation is supplied with.

In the configuration according to the present invention, the heavy particles eventually settled at the lower level of the tank 1 are, upon opening the valve 9, taken along by gravity in the flow of material, preferably in a first phase of extraction. The flow corresponding to this first phase is thus directed towards the device 10 allowing the discharge of the digested material.

On the other hand, in order to spawn the products before their entering into the tank 1, a circuit for re-circulating 11 part of the digested material towards the supply openings 2 is provided for.

In this respect, it is recalled that according to the spirit of the invention, the latter seeks for a uniform circulation of the material in the tank. It is then possible to contemplate to control the speed of circulation of the material in the tank.

Since the process and device according to the invention refer to a continuous-digestion process and device, the result is that for a given quantity of material entering into the system is extracted an equivalent quantity of digested material.

Thus, another advantageous feature of this invention consist in conferring to said material, during the recycling of the fermented material at a high flow rate, a high circulation speed so as to take along the heavy particles eventually settled in the pipes.

The installation for implementing the process according to the invention comprises, for the recirculation circuit 11, a connection external to the tank 1, intervening between the discharge means 3 and the means 2 for supplying material to be treated.

According to a feature of the invention shown in FIG. 6, at least one exit opening 3D is connected to a storage device 12, operating at atmospheric pressure, consisting of a feed hopper located on a supply pump 13, via a pipe 14 equipped with at least one automatically controlled valve 15. The opening of this valve 15 allows direct communication between the fermentation tank and the buffer storage formed by the device 12.

Thus the static pressure generated by the height H of the material under fermentation in the tank 1 is transmitted directly to the material inside the pipe 14.

By choosing the diameter of the pipes appropriately is achieved a very high material flow-rate during the period of opening of said valve 15, much higher than the flow rate that could be ensured with only a pump of the same type as that being used for supplying the material. This high flow rate generates a high speed of circulation of the material, so that the heavy particles eventually settled are taken along in the flow of material. An obstruction of the pipes is thus avoided.

A suitable sequence of successive opening and closing of the valve permits to achieve high flow rates over short periods of time and, hence, punctually a high speed of circulation of the material in the pipes, while guaranteeing a selected resulting average flow rate.

To enhance the control of the flow rate, a pump can nevertheless advantageously complete this device.

What is claimed:

1. Process for anaerobic treatment of material with a high solid concentration higher than 15%, in a digester in the form of a closed tank provided with means for supplying material to be treated and means for discharging the digested material as well as means for vertical homogenisation in the form of gaseous-fluid injectors on the bottom of the tank, wherein, through a distribution at the level of the tank of the means for supplying material with respect to the discharge means and through the means for vertical homogenisation guaranteeing the homogeneity of the material by vertical sectors in the tank, a uniform forced unidirectional circulation is imparted to the material in the tank over the full cross-section of the latter, and according to a substantially horizontal component, between said supply means and said discharge means.

2. Process for anaerobic treatment of material with a high solid concentration in a digester in the form of a closed tank according to claim 1, the internal space of said tank being divided into vertical sectors by the arrangement of the homogenisation means, wherein the vertical sectors are homogenized intermittently and successively by the homogenisation means.

3. Process for anaerobic treatment of material with a high solid concentration in a digester in the form of a closed tank according to claim 1, wherein a preferred extraction of the settled particles is carried out at the bottom of the tank.

4. Process for anaerobic treatment of material with a high solid concentration in a digester in the form of a closed tank according to claim 1, wherein a recirculation of the material is performed between the discharge means and the supply means.

5. Process for anaerobic treatment of material with a high solid concentration in a digester in the form of a closed tank according to claim 4, wherein the recirculation of the material is performed between the discharge means and the supply means for short periods of time.

6. Installation for implementing the process according to claim 1, comprising a digester in the form of a closed tank provided with means for supplying material to be treated and means for discharging the digested material as well as means for vertical homogenisation in the form of gaseous-fluid injectors on the bottom of the tank, wherein the means for supplying material are arranged at the level of the tank diametrically opposite the means for discharging the digested material, and, in combination, the means for vertical homogenisation are comprised of gaseous-fluid injection ramps extending in the bottom of the tank transversely to the substantially horizontal direction of flow of material in the tank.

7. Installation according to claim 6, comprising a digester in the form of a closed cylindrical tank, wherein the means for supplying material and the means for discharging digested material are arranged according to an arc of a circle over the circular cross-section of the tank.

8. Installation according to claim 6, comprising a digester in the form of a closed cylindrical tank, wherein the means for supplying the material and the means for discharging the digested material are arranged at different heights of the tank.

9. Installation according to claim 6, comprising a digester in the form of a closed tank provided with vertical homogenisation means, wherein the gaseous-fluid injectors are arranged on ramps parallel to each other and perpendicular to the direction of advancing of the material in the tank.

10. Installation according to claim 6, wherein the installation comprises in addition a device for discharging the digested material, in particular a device permitting their additional dehydration.

11. Installation according to claim 6, wherein the installation comprises in addition a circuit for re-circulating the material between the discharge means and the supply means.

* * * * *